United States Patent [19]

Tsolis et al.

[11] 4,435,533

[45] Mar. 6, 1984

[54] 4-HYDROXY-5-(SUBSTITUTED PHOSPHINYL)ETHYLENEUREAS

[76] Inventors: Alexandros K. Tsolis, 171 Old National Rd., Arachovitika; Ioannis A. Mikroyannidis, Navmahias Elis 48-52, both of Patra, Greece

[21] Appl. No.: 288,473

[22] Filed: Jul. 30, 1981

[51] Int. Cl.³ .............................................. C07F 9/65
[52] U.S. Cl. ................................ 524/106; 106/18.15; 106/176; 548/111
[58] Field of Search .................. 548/111; 524/106; 106/18.15, 18.18, 18.21, 177, 176

[56] References Cited

U.S. PATENT DOCUMENTS 4,237,122  12/1980  Asao et al. ...................... 548/111 X

*Primary Examiner*—Richard Raymond
*Attorney, Agent, or Firm*—Hubbell, Cohen, Stiefel & Gross

[57] ABSTRACT

This invention relates to novel 4-hydroxy-5-(substituted phosphinyl)ethyleneureas of the general Formula I

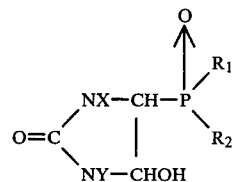

to methods of making the same, to flame resistant compositions containing such compounds and to the use of compositions containing such compounds to impart flame resistance to cellulose and cellulose containing materials.

In the compounds of the Formula I X or Y may be hydrogen or alkyl, $R_1$ and $R_2$ may be the same or different radicals including alkoxy, cycloalkoxy, aryloxy, arylalkoxy, alkyl, aryl as well as such radicals containing substituents such as halogen; in addition, $R_1$ and/or $R_2$ may be hydroxy.

9 Claims, No Drawings

4-HYDROXY-5-(SUBSTITUTED PHOSPHINYL)ETHYLENEUREAS

SUMMARY OF THE INVENTION

This invention relates to novel 4-hydroxy-5-(substituted phosphinyl)ethyleneureas of the general Formula I

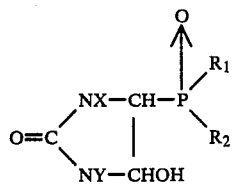

to methods of making the same, to flame resistant compositions containing such compounds and to the use of compositions containing such compounds to impart flame resistance to cellulose and cellulose containing materials.

In the compounds of the Formula I X or Y may be hydrogen or alkyl, $R_1$ and $R_2$ may be the same or different radicals including alkoxy, cycloalkoxy aryloxy, arylalkoxy, alkyl, aryl as well as such radicals containing substituents such as halogen in addition $R_1$ and/or $R_2$ may be hydroxy.

We have discovered that these novel compounds may be prepared in good yields by reacting in a mole ratio close to 1 urea or a monoalkyl urea with 2-hydroxy-2-phosphinyl ethanals of the general Formula II

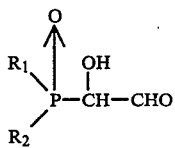

produced according to the method of our pending patent application Ser. No. 288,607, which is incorporated by reference herein, wherein $R_1$ and $R_2$ may be the same or different radicals including alkoxy, cycloalkoxy, aryloxy, arylalkoxy, alkyl, aryl as well as such radicals containing substituents such as halogen. The following are illustrative of the phosphinyl ethanals which may be employed as reactants in the procedure: 2-hydroxy-2-(dimethoxy phosphinyl)ethanal, 2-hydroxy-2-(diethoxyphosphinyl)ethanal, 2-hydroxy-2-(diisopropoxyphosphinyl)ethanal, 2-hydroxy-2-[di(n-butoxy)phosphinyl]ethanal, 2-hydroxy-2-[di(2-chloroethoxy)phosphinyl]ethanal, 2-hydroxy-2-(diphenoxyphosphinyl)ethanal.

The reaction is carried out by contacting under stirring the reactants in a reaction medium consisting of a solvent or solvent mixtures in which the reactants are at least partly soluble and by maintaining the temperature of the reaction mixture between 40°–80° C. until the reaction is completed. The solvents which may be employed are: methanol, ethanol, acetonitrile, water etc. The choice of the solvent or the solvent mixtures will be governed by such factors as solubility of the reactants, economy for the particular application and ease of recovery of the product as well as many other considerations. In all instances, however, the solvents used should be substantially non reactive with the reactants and the products under the prevalent reaction conditions. The initial pH of the reaction mixture is governed by the reactants being present. The preferred range of pH is between 2 and 4.

The novel compounds of the general Formula I wherein $R_1$ and/or $R_2$ are hydroxy radicals are produced by heating the compounds of Formula I wherein $R_1$ and/or $R_2$ are alkoxy, arylalkoxy or aryloxy radicals in water medium or in such a medium made acidic with a acid such as hydrochloric acid.

The invention includes within its scope flame resistant compositions which contain in various ratios at least one compound of the general Formula I preferably of these wherein $R_1$ and $R_2$ are the same alkoxy radicals of up to four carbon atoms or such radicals containing substituents such as chlorine or bromine and one of the polymeric materials including polyamides such as poly(hexamethylene adipamide), poly(hexamethylene sebacamide), poly(6-aminocaproic acid) and the like, polyesters such as poly(ethylene terephthalate) and the like, polyurethanes such as poly(ethylene-2,4-tolylene urethane) and the like, polyethylene, polystyrene or blends of polymeric materials.

The invention includes within its scope compositions of utility in imparting flame-resistance and crease-resistance to cellulose or cellulose containing materials, fibers and/or fabrics, which contain at least one compound of the general Formula I preferably of these wherein $R_1$ and $R_2$ are the same alkoxy radicals of up to four carbon atoms or such radicals containing substituents such as chlorine or bromine. Such compositions contain also an alkaline compound such as sodium hydroxide to render the compound of the Formula I soluble in water. These compositions designated with the letter A are used in combination with compositions designated with the letter B containing an aminoplast and an acid catalyst to accelerate the reaction of the compound of the general Formula I with the aminoplast and/or the cellulose, curing and crosslinking of the aminoplast and/or its reaction products with compound of the general Formula I. The acid catalyst which may be used, are well known in the process of curing aminoplast on cellulosic materials and include for example phosphoric acid, ammonium dihydrogen phosphate, ammonium chloride, boric acid, etc. Suitable aminoplast include condensation products of formaldehyde with urea or a derivative thereof such as ethyleneurea or dihydroxyethyleneurea or preferably, with melamine or a derivative such as an ether of the said melamine-formaldehyde condensation product and the like. The components of the compositions can be employed in varying ratios and concentrations and preferably in water solution or in solvent or solvent mixtures in which they are soluble and which they may not cause adverse effects to the application. A process for rendering cellulose containing materials flame resistant and crease-resistant including impregnation of the cellulose containing material with composition A, to a certain weight increase followed by drying, impregnation with composition B to a certain weight increase and heating the treated material to cure the compound of the general Formula I or its reaction product with the aminoplast and/or to effect crosslinking is within the scope of the invention.

The invention will be further illustrated by the following specific examples. It should be understood, however that while these examples may describe specific features of the invention they are presented primarily for the purpose of illustration and the invention in its broader aspects is not limited thereto.

EXAMPLE 1

4-Hydroxy-5-(dimethoxyphosphinyl)ethyleneurea

Glyoxal trimer dihydrate and dimethyl phosphite in a mol ratio 0.33:1.2 respectively were introduced in a reaction flask equipped with a side condenser. The reaction mixture was heated under stirring with an oil bath maintained at 110° C. while the pressure over the reaction mixture was 80 mmHg. The released water was distilled together with a small portion of dimethyl phosphite. After a reaction time of 12 min the remaining liquid product was cooled with an ice bath. 150 ml of methanol and 1 mol of urea per mol of crude product was added. The solution was heated at 50° C. for 60 min. Precipitation of 4-hydroxy-5-(dimethoxyphosphinyl)ethyleneurea occured during the course of the reaction and was completed by cooling: overall yield 30%, m.p. 140°–141° C. dc after recrystallization from dimethylformamide-dioxane 1:1, V:V. Anal.Calcd for $C_5H_{11}N_2O_5P$: C, 25.58; H, 5.28; N, 13.33. Found: C, 28.71; H, 5.44; N, 13.15.

EXAMPLE 2

4-Hydroxy-5-(diethoxyphosphinyl)ethyleneurea

Glyoxal trimer dihydrate and diethyl phosphite in a mole ratio 0.33:1.1 respectively together with 750 ml dioxane per mol of glyoxal trimer dihydrate were introduced in a reaction flask equipped with a side condenser. The reaction mixture was heated under stirring with an oil bath for 35 min., during which time the released water was distilled together with dioxane at atmospheric pressure in a slow rate. The reaction mixture was cooled to 40° C. and the volatile components were removed by a rotary evaporator at this temperature. 300 ml of ethanol and 1 mol of urea per mol of crude phosphinyl ethanal was added. The resulting solution was heated at 50° C. for 60 min. Precipitation of 4-hydroxy-5-(diethoxyphosphinyl)ethyleneurea occured during the course of the reaction and was completed by cooling: overall yield 50%, m.p. 151°–152° C. of the recrystallization from ethanol:water 4:1, V:V. Anal. Calcd for $C_7H_{15}N_2O_5P$: C, 35.29; H, 6.35; N, 11.76. Found: C, 35.53; H, 6.43; N, 12.05.

EXAMPLE 3

4-Hydroxy-5-(diethoxyphosphinyl)ethyleneurea

The method of the Example 2 was applied with the exception that 500 ml of water per mol of crude phosphinyl ethanal was used as a reaction solvent. A 60% yield was obtained.

EXAMPLE 4

4-Hydroxy-5-(diisopropoxyphosphinyl)ethyleneurea

Glyoxal trimer dihydrate and diisopropyl phosphite in a mol ratio 0.33:1.2 respectively together with 750 ml of dioxane per mol of glyoxal trimer dihydrate were introduced in a reaction flask equipped with a side condenser. The reaction mixture was heated under stirring with an oil bath for 55 min during which time the released water distilled together with dioxane in a slow rate. The reaction mixture was cooled to 40° C. and the volatile components were removed by a rotary evaporation under aspirator vacuo at this temperature. 500 ml of water and 1 mol of urea per mol of the crude phosphinyl ethanal was added. The resulted solution was heated at 50° C. for 60 min. Precipitation of 4-hydroxy-5-(diisopropoxyphosphinyl)ethyleneurea occured during the course of the reaction and was completed by cooling:overall yield 55%, m.p. 201°–202° C. dc after recrystallization from water-isopropanol 2:1, V:V. Anal. Calcd for $C_9H_{19}N_2O_5P$: C, 40.60; H, 7.19; N, 10.52. Found: C, 40.85; H, 6.91; N, 10.24.

EXAMPLE 5

4-Hydroxy-5-[di(n-butoxy)phosphinyl]ethyleneurea

For the preparation of 2-hydroxy-2-[di(n-butoxy phosphinyl]ethanal glyoxal trimer dihydrate reacted with di(n-butyl)phosphite according to the procedure of Example 2. 200 ml of a mixture of water and acetonitrile 14:6, V:V and 1 mol of urea per mol of the phosphinyl ethanol was added. The resulting solution was heated at 50° C. for 60 min. Precipitation of 4-hydroxy-5-[di(n-butoxy)phosphinyl]ethyleneurea during the course of the reaction and after cooling gave a 30% yield, m.p. 146°–148° C. after recrystallization from acetonitriledioxane 3:1, V:V. Anal. Calcd for $C_{11}H_{23}N_2O_5P$: C, 44.89; H, 7.88; N, 9.52. Found: C, 44.70; H, 7.80; N, 9.32.

EXAMPLE 6

4-Hydroxy-5-[di-(2-chloroethoxy)phosphinyl]ethyleneurea

For the preparation of 2-hydroxy-2-[di(2-chloroethoxy)phosphinyl]ethyleneurea glyoxal trimer dihydrate reacted with di(n-chloroethyl)phosphite according to the procedure of Example 2. 500 ml of water and 1 mol of urea per mol of the crude phosphinyl ethanol was added. The resulting solution was heated at 50° C. for 60 min. Precipitation of 4-hydroxy-5-[di(2-chloroethoxy)phosphinyl]ethyleneurea occured during the course of the reaction and after cooling afforded a 55% yield, m.p. 141°–142° C. after recrystallization from ethanol-water 8:2, V:V. Anal. Calcd for $C_7H_{13}Cl_2N_2O_5P$: C, 27.39; H, 4.24; N, 9.13. Found: C, 27.56; H, 4.55; N, 9.05.

EXAMPLE 7

4-Hydroxy-5-(diphenoxyphosphinyl)ethyleneurea 7.0 g (0.03 mol) of glyoxal trimer dihydrate and 51.5 g (0.22 mol) of diphenyl phosphite were introduced in a reaction flask equipped with a side condenser. The reaction mixture was heated under stirring with an oil bath maintained at 80° C. for 50 min during which time the released water together with a small portion of phosphite were distilled in a slow rate under aspirator vacuo. The mixture was cooled to 40° C. and the volatile components were removed under aspirator vacuo at this temperature. 200 ml of water and 1 mol of urea per mol of the crude phosphinyl ethanal was added. The resulted solution was heated at 50° C. for 60 min. Precipitation of 4-hydroxy-5-(diphenoxyphosphinyl)ethyleneurea occured during the course of the reaction and was completed by cooling of the reaction mixture. A 20% yield was obtained m.p. 175°–176° C. after recrystallization from acetonitrile-dimethylformamide 1,5:1, V:V. Anal. Calcd C, 53.89; H, 4.52; N, 8.38. Found: C, 53.98; H, 4.76; N, 8.19.

EXAMPLE 8

4-Hydroxy-5-(dihydroxyphosphinyl)ethylenenurea

This example demonstrates the preparation of 4-hydroxy-5-(dihydroxyphosphinyl)ethyleneurea by hydrolysis of 4-hydroxy-5-(diethoxyphosphinyl)ethyleneurea according to the method of the invention. 0.5 g of 4-hydroxy-5-(diethoxyphosphinyl)ethyleneurea and 15 ml of 10% of hydrochloric acid were introduced into a round bottom flask. The mixture was refluxed until a solution was obtained. After the removal of the volatile components of the mixture under vacuo, a nearly quantitative yield of 4-hydroxy-5-(dihydroxyphosphinyl)ethyleneurea was obtained: Anal. Calcd for $C_3H_7N_2O_5P$: C, 19.79; H, 3.88; N, 15.39. Found: C, 19.62; H, 3.93; N, 15.42.

EXAMPLE 9

4-Hydroxy-1-methyl-5-(diethoxyphosphinyl)ethyleneurea and 4-hydroxy-3-methyl-5-(diethoxyphosphinyl)ethyleneurea.

41.63 g of crude 2-hydroxy-2-(diethoxyphosphinyl)ethanal prepared from the reaction of glyoxal trimer dihydrate and diethyl phosphite according to the Example 2 reacted under stirring with 14.82 g (200 mmol) N-methyl urea in 45 ml of ethanol by heating the solution at 50° C. for 60 min. Addition of ether caused the precipitation of a white solid which, as shown spectroscopically was a mixture of 4-hydroxy-1-methyl-5-(diethoxyphosphinyl)ethyleneurea and 4-hydroxy-3-methyl-5-(diethoxyphosphinyl)ethyleneurea in a ratio 18:82 respectively. Overall yield 40%, m.p. 154°–155° C. after recrystallization from ethanol-ether 2:1, V:V. Anal. Calcd for $C_8H_{17}N_2PO_5$: C, 38.09; H, 6.79; N, 11.11. Found: C, 37.79; H, 6.48; N, 10.98.

EXAMPLE 10

The organophosphorus compounds of the general Formula I of the present invention are useful as fire retardants. The following examples illustrate some the uses of typical products.

Examples of fire retardant and crease improving compositions as well as of finishing procedures of cotton fabrics with them and the methods of testing used are reported below:

Finishing compositions $I_A$ 23.5 parts of 4-hydroxy-5-(dimethoxyphosphinyl)ethyleneurea, 27.8 parts of 20% sodium hydroxide solution and 48.7 parts water.

$I_B$ 45.7 parts of trimethylolmelamine (TMM) solution 40% by weight, 11.4 parts of phosphoric acid solution 85% by weight, 1.0 part of surfactant and 41.9 parts of water.

$II_A$ 21.0 parts of 4-hydroxy-5-(diethoxyphosphinyl)ethyleneurea, 24.8 parts of 20% sodium hydroxide solution and 54.2 parts of water.

$II_B$ 49.0 parts of TMM solution 40% by weight, 9.8 parts of phosphoric acid solution 85% by weight, 1.0 part of surfactant and 40.2 parts of water.

$III_A$ 23.5 parts of 4-hydroxy-5-[di(2-chloroethoxy)phosphinyl]ethyleneurea, 27.8 parts of 20% sodium hydroxide solution and 48.7 parts of water.

$III_B$ 50.3 parts of TMM solution 40% by weight, 7.5 parts of phosphoric acid solution 85% by weight. 1.0 part of surfactant and 41.2 parts of water.

Finishing procedures and testing

The characteristic of the unfinished cotton fabric were the following: weight 122 g/m², recovery angle 161°, breaking load of the specimens cut parallely to the warp yarns 65 kg/cm and of the specimens cut parallely to the weft yarns 35 kg/cm.

Specimens of the above mentioned cotton fabric are padded first in one of the compositions $I_A$, $II_A$ or $III_A$ to a certain weight increase, dried by a stream of hot air at 80° C., then padded in the corresponding composition $I_B$, $II_B$ or $III_B$ to a certain weight increase dried and cured at 160° C. for 10 min. They are washed for 10 min at 60° C. with a 20% aqueous sodium bicarbonate solution, rinsed with water and dried. The flame resistance was measured by the AATCC 34-1966 method. The crease resistance was measured by the AATCC 66-1975 method and the breaking load according to ASTM D 1682-64. The results are shown in Table I.

TABLE I

Cotton fabric finishing by I. 4-hydroxy-5-dimethoxyphosphinylethyleneurea, II. 4-hydroxy-5-diethoxyphosphinylethyleneurea and III. 4-hydroxy-5-di(2-chloroethoxy)-phosphinylethyleneurea. Warp specimens i, weft specimens ii.

| Specimens | Pick up of A composition % | Pick up of B composition % | Char length cm | Recovery angle degrees | Breaking load kg/cm |
|---|---|---|---|---|---|
| $I_i$ | 122 ± 1 | 63 ± 4 | 9.1 ± 0.2 | 198 ± 3 | 37 ± 2 |
| $I_{ii}$ | 127 ± 6 | 66 ± 4 | 8.8 ± 0.1 | 201 ± 3 | 16 ± 2 |
| $II_i$ | 128 ± 3 | 96 ± 5 | 7.8 ± 0.5 | 231 ± 3 | 45 ± 1 |
| $II_{ii}$ | 136 ± 2 | 106 ± 3 | 7.1 ± 0.1 | 230 ± 3 | 15 ± 2 |
| $III_i$ | 126 ± 2 | 93 ± 4 | 8.2 ± 0.5 | 228 ± 3 | 36 ± 2 |
| $III_{ii}$ | 131 ± 4 | 96 ± 2 | 7.0 ± 0.4 | 234 ± 2 | 15 ± 3 |

The compounds of the general Formula I are useful as additives for the preparation of fire resistant compositions. These uses are demonstrated by the following examples:

Powders of 4-hydroxy-5-(diethoxy-phosphinyl)ethyleneurea and separately of 4-hydroxy-5-[di(2-chloroethoxy)phosphinyl]ethyleneurea were mixed with powder of poly($\epsilon$-caprolactam) in the percentages shown in Table II and in Table III. The Limiting Oxygen Index of the specimens formed by hot-pressing in a mold were determined by the method ASTM D 2863-70 and showed that the blends had increased fire resistance in comparison to the heat polymer as shown in Table II and in Table III.

TABLE II

Effect of 4-hydroxy-5-(diethoxyphosphinyl)ethyleneurea as a fire retardant additive to poly($\epsilon$-caprolactam).

| Additive % | 0 | 8.46 | 12.69 | 16.54 | 25.00 | 33.08 |
|---|---|---|---|---|---|---|
| P % | 0 | 1.10 | 1.65 | 2.15 | 3.25 | 4.30 |
| LOI | 20.8 | 22.8 | 24.8 | 27.0 | 27.2 | 27.2 |

TABLE III

Effect of 4-hydroxy-5-di(2-chloroethoxy)phosphinylethyleneurea as a fire retardant additive to poly($\epsilon$-caprolactam).

| Additive % | 0 | 4.16 | 8.33 | 16.66 | 25.00 |
|---|---|---|---|---|---|
| P % | 0 | 0.42 | 0.84 | 1.68 | 2.52 |
| Cl % | 0 | 0.96 | 1.93 | 3.85 | 5.78 |
| LOI | 20.8 | 24.7 | 25.5 | 26.9 | 28.2 |

We claim:

1. A compound of the formula:

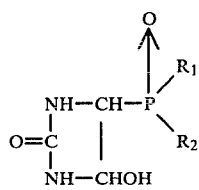

wherein $R_1$ and $R_2$ are selected from the group consisting of alkoxy of 1 to 4 carbon atoms, cyclohexyloxy, phenoxy, alkoxy containing chlorine, alkoxy containing bromine and hydroxy.

2. A compound of the formula:

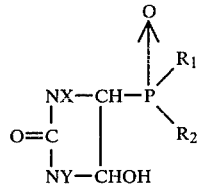

wherein X and Y are both hydrogen or hydrogen and alkyl of 1 to 4 carbon atoms and wherein $R_1$ and $R_2$ are selected from the group consisting of alkoxy of 1 to 4 carbon atoms, cyclohexyloxy, phenoxy, alkoxy containing chlorine, alkoxy containing bromine and hydroxy.

3. A method of making the compound of claim 1 comprising reacting in a solvent or in solvent mixtures which are substantially non-reactive with the reacting compounds and at a pH 2 to 4 urea with 2-hydroxy-2-(substituted phosphinyl)ethanal of the formula

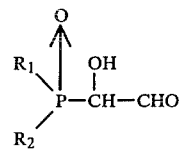

wherein $R_1$ and $R_2$ are radicals defined in claim 1, in a mol ratio close to 1.

4. A method of making the compounds of claim 2 comprising reacting in a solvent or in solvent mixtures which are substantially non-reactive with the reacting compounds and at a pH 2 to 6 monoalkyl urea XNHC(C)NH$_2$ wherein X is alkyl of 1 to 4 carbon atoms with 2-hydroxy-2-(substituted phosphinyl)ethanals of the formula

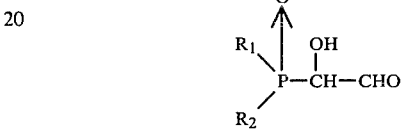

wherein $R_1$ and $R_2$ are radicals defined in claim 2 in a mol ratio close to 1.

5. A method of fire-proofing a polymeric material selected from the group consisting of cellulose, cellulose containing material, polyamides, polyurethanes, polyesters and polyacrylonitriles, which comprises incorporating into the polymeric material the compounds of claim 1 or 2.

6. The method of claim 5, wherein the incorporation is carried out in the presence of a solvent.

7. The method of claim 5, wherein the cellulose of the cellulose containing material is impregnated in alkaline solution, dried, impregnated in an aqueous solution containing an amino plast, an acidic catalyst and a surfactant, dried and cured.

8. The method of claim 7, wherein the cellulose containing material is cotton fabric.

9. The method of claim 7, wherein the cellulose containing material is paper.

* * * * *

UNITED STATES PATENT AND TRADEMARK OFFICE
CERTIFICATE OF CORRECTION

PATENT NO. : 4,435,533
DATED : March 6, 1984
INVENTOR(S) : Alexandros K. Tsolis and Ioannis A. Mikroyannidis It is certified that error appears in the above—identified patent and that said Letters Patent is hereby corrected as shown below:

Column 3, line 22: "25.58" should read --28.58--.

Column 8, line 15: "XNHC(C)NH$_2$" should read --XNHC(O)NH$_2$--.

Signed and Sealed this

Twenty-fifth Day of September 1984

[SEAL]

Attest:

GERALD J. MOSSINGHOFF

Attesting Officer    Commissioner of Patents and Trademarks